US012508172B2

(12) United States Patent
Key et al.

(10) Patent No.: US 12,508,172 B2
(45) Date of Patent: Dec. 30, 2025

(54) REUSABLE DIAPER WITH DISPOSABLE PAD DEVICE

(71) Applicants: Rachelle Key, Section, AL (US); Roxanne Frederick, Grant, AL (US)

(72) Inventors: Rachelle Key, Section, AL (US); Roxanne Frederick, Grant, AL (US)

( * ) Notice: Subject to any disclaimer, the term of this patent is extended or adjusted under 35 U.S.C. 154(b) by 388 days.

(21) Appl. No.: 17/871,159

(22) Filed: Jul. 22, 2022

(65) Prior Publication Data

US 2023/0025439 A1 Jan. 26, 2023

Related U.S. Application Data

(60) Provisional application No. 63/224,917, filed on Jul. 23, 2021.

(51) Int. Cl.
*A61F 13/49* (2006.01)

(52) U.S. Cl.
CPC .... *A61F 13/49004* (2013.01); *A61F 13/4906* (2013.01); *A61F 13/49003* (2013.01); *A61F 13/49006* (2013.01)

(58) Field of Classification Search
CPC ............ A61F 13/4906; A61F 13/49004; A61F 13/49006; A61F 13/49003
USPC .................................. 604/385.185, 363, 364
See application file for complete search history.

(56) References Cited

U.S. PATENT DOCUMENTS

| | | | | |
|---|---|---|---|---|
| 6,716,441 B1 * | 4/2004 | Osborne | A61L 15/46 | 424/404 |
| 2007/0287983 A1 * | 12/2007 | Lodge | A61F 13/66 | 604/392 |
| 2008/0215028 A1 * | 9/2008 | Brown | A61F 13/505 | 604/385.15 |
| 2008/0319407 A1 * | 12/2008 | Erdem | D04H 1/74 | 28/104 |
| 2010/0179500 A1 * | 7/2010 | Roe | A61F 13/74 | 604/386 |

* cited by examiner

*Primary Examiner* — Jacqueline F Stephens
(74) *Attorney, Agent, or Firm* — Brennan, Manna & Diamond, LLC

(57) ABSTRACT

The present invention relates to a reusable diaper with a disposable pad device primarily comprised of a body that has an outer surface, an inner surface with at least one pad and a rear surface and a front surface each with at least two tabs. The tabs allow the device to be secured around the user. The pad is further removably-attached to the inner surface via at least one fastener, such that the pad can be removed when a user soils and/or defecates in the device. The top surface of the pad is further comprised of a gel pad and infused with lotion, such that it does not irritate the skin of the user. Therefore, a user can replace the pad when necessary, while continuing to utilize the rest of the device for multiple diaper changes.

17 Claims, 3 Drawing Sheets

REUSABLE DIAPER WITH DISPOSABLE PAD DEVICE

CROSS-REFERENCE TO RELATED APPLICATION

The present application claims priority to, and the benefit of, U.S. Provisional Application No. 63/224,917, which was filed on Jul. 23, 2021 and is incorporated herein by reference in its entirety.

FIELD OF THE INVENTION

The present invention relates generally to the field of diapers. More specifically, the present invention relates to a reusable diaper with a disposable pad device. The pad is further removably-attached to the inner surface via at least one fastener, such that the pad can be removed when a child soils/defecates in the device. The top surface of the pad may further be comprised of a gel pad and infused with lotion, such that it does not irritate the skin of the user. Therefore, a user can replace the pad when necessary while continuing to utilize the rest of the body of the device for multiple diaper changes. Accordingly, the present disclosure makes specific reference thereto. Nonetheless, it is to be appreciated that aspects of the present invention are also equally applicable to other like applications, devices and methods of manufacture.

BACKGROUND

Typically, infants, children and adults with special needs may wear diapers on a daily basis. However, parents and guardians may have limited access to diapers due to supply issues or due to the lack of financial ability to purchase diapers. Therefore, some parents may be forced to reuse disposable diapers, which is unsanitary and can lead to skin conditions and/or infections. As an alternative, parents may purchase cloth diapers that can be washed and reused. However, some parents may find this option equally unsanitary, and also may not desire to wash a soiled cloth diaper.

Therefore, there exists a long-felt need in the art for an improved reusable diaper. There also exists a long-felt need in the art for a reusable diaper with a disposable pad device that combines the benefits of reusable cloth diapers and disposable diapers. In addition, there exists a long-felt need in the art for a reusable diaper with a disposable pad device that can be re-used after being soiled, without posing a risk of skin infection or irritation to the user.

The subject matter disclosed and claimed herein, in one embodiment thereof, comprises a reusable diaper with a disposable pad device. The device is primarily comprised of a body that has an outer surface and an inner surface, a rear surface with at least two tabs, a front surface with at least two tabs and an inner surface with at least one pad. The tabs of the device allow the device to be secured around a user's body. The pad is further removably-attached to the inner surface via at least one fastener, such that the pad can be removed when a user soils/defecates in the device. The top surface of the pad may further be comprised of a gel pad and infused with lotion, such that it does not irritate the user's skin. In addition, the edges of the pad may be perforated, such that urine and/or feces cannot spill from the pad when the pad is removed from the inner surface. Therefore, a user can replace the pad when necessary, while continuing to utilize the rest of the device for multiple diaper changes.

In this manner, the reusable diaper with disposable pad device of the present invention accomplishes all of the forgoing objectives and provides an improved diaper. The device further combines the benefits of disposable and reusable diapers, as portions of the device can be reused and also disposed of as necessary. Further, the reusable portion of the device does not pose a risk of skin infection or irritation to the user.

SUMMARY

The following presents a simplified summary in order to provide a basic understanding of some aspects of the disclosed innovation. This summary is not an extensive overview, and it is not intended to identify key/critical elements or to delineate the scope thereof. Its sole purpose is to present some general concepts in a simplified form as a prelude to the more detailed description that is presented later.

The subject matter disclosed and claimed herein, in one embodiment thereof, comprises a reusable diaper with disposable pad device. The device is primarily comprised of a body that has an outer surface and an inner surface, a rear surface with at least two tabs, a front surface with at least two tabs and an inner surface with at least one pad. In differing embodiments, the body of the device may be made of a plurality of suitable materials as is known in the art. Further, the body and/or other components of the device may be infused with a plurality of moisturizing substances and may also be hypoallergenic and scented or non-scented. In addition, the body has two continuous leg openings to allow the legs of a user to be placed through the body, while the device is in use. The at least two tabs of the rear surface and the front surface are further each comprised of at least one fastener that allows the tabs to adhere to one another, such that the body of the device can be secured around a user.

The pad of the device is preferably absorbent. Further, the bottom surface of the pad is comprised of at least one fastener, such that the pad can be removably-attached to the inner surface and can be removed from the inner surface and replaced with another pad, when an infant urinates and/or defecates on the pad. The top surface of the pad may further have at least one gel pad that increases the comfort of the top surface against a user's skin. In addition, the top surface may further be infused with or may be coated with a lotion that prevents diaper rash, irritation and infection. In one embodiment, the top surface and/or bottom surface may further be manufactured from a moisture-wicking material. Further, the bottom surface is also preferably impermeable, such that any urine and/or feces cannot seep through the pad and into the inner surface. The edges of the pad may further be raised and/or pleated to prevent urine and/or feces from spilling out from the pad and onto the inner surface when the pad is removed.

Accordingly, the reusable diaper with disposable pad device of the present invention is particularly advantageous as it provides an improved diaper that combines the benefits of disposable and reusable diapers by allowing portions of the device to be reused and/or disposed of as necessary. Further, the reusable portion of the device does not pose a risk of skin infection or irritation to the user. In this manner, the reusable diaper with disposable pad device overcomes the limitations of existing diapers known in the art by offering features not available with existing reusable and/or disposable diapers.

To the accomplishment of the foregoing and related ends, certain illustrative aspects of the disclosed innovation are described herein in connection with the following description and the annexed drawings. These aspects are indicative, however, of but a few of the various ways in which the principles disclosed herein can be employed and are intended to include all such aspects and their equivalents. Other advantages and novel features will become apparent from the following detailed description when considered in conjunction with the drawings.

BRIEF DESCRIPTION OF THE DRAWINGS

The description refers to provided drawings in which similar reference characters refer to similar parts throughout the different views, and in which.

DETAILED DESCRIPTION

Figure 1:
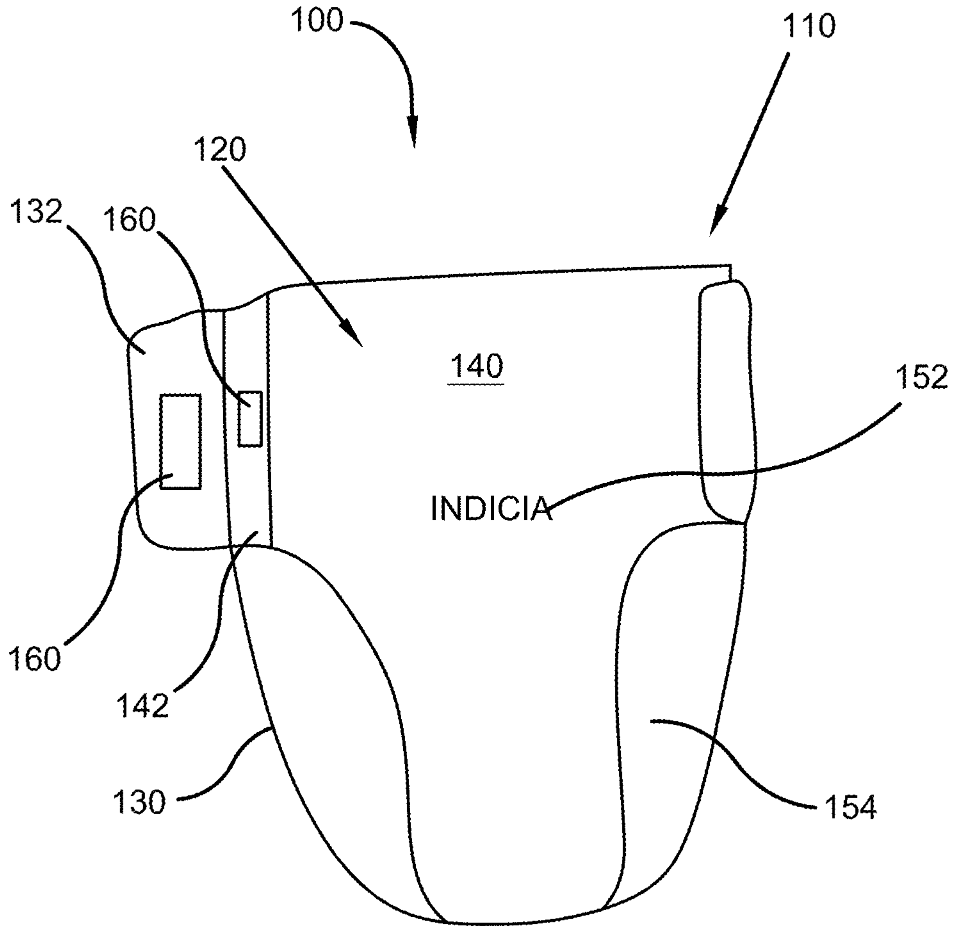
FIG. 1 illustrates a front view of one potential embodiment of the reusable diaper with disposable pad device of the present invention in accordance with the disclosed architecture.

The innovation is now described with reference to the drawings, wherein like reference numerals are used to refer to like elements throughout. In the following description, for purposes of explanation, numerous specific details are set forth in order to provide a thorough understanding thereof. It may be evident, however, that the innovation can be practiced without these specific details. In other instances, well-known structures and devices are shown in block diagram form in order to facilitate a description thereof. Various embodiments are discussed hereinafter. It should be noted that the figures are described only to facilitate the description of the embodiments. They are not intended as an exhaustive description of the invention and do not limit the scope of the invention. Additionally, an illustrated embodiment need not have all the aspects or advantages shown. Thus, in other embodiments, any of the features described herein from different embodiments may be combined.

As noted above, there is a long-felt need in the art for an improved reusable diaper. There also exists a long-felt need in the art for a reusable diaper with a disposable pad device that combines the benefits of reusable cloth diapers and disposable diapers. In addition, there exists a long-felt need in the art for a reusable diaper with disposable pad device that can be re-used after being soiled, without posing a risk of skin infection or irritation to the user.

The present invention, in one exemplary embodiment, is comprised of a reusable diaper with disposable pad device, primarily comprised of a body that has an outer surface and an inner surface, a rear surface with at least two tabs, a front surface with at least two tabs and an inner surface with at least one pad. In differing embodiments, the body of the device may be manufactured of a plurality of materials as is known in the art. The body and/or all of the components of the device may be infused with a plurality of moisturizing substances, and may also be hypoallergenic and scented or non-scented. In addition, the body has two continuous leg openings to allow the legs of a user to be placed through while the device is in use. The at least two tabs of the rear surface and the front surface are further each comprised of at least one fastener that allows the tabs to adhere to one another, such that the body of the device can be secured around a user.

The pad of the device is preferably absorbent. Further, the bottom surface of the pad is comprised of at least one fastener, such that the pad can be removably-attached to the inner surface and can be removed from the inner surface and replaced with another pad, when a user urinates and/or defecates on the pad. The top surface of the pad may further have at least one gel pad that increases the comfort of the surface against a user's skin and may be infused with or may be coated with a lotion that prevents diaper rash, irritation and infection. The top surface and/or bottom surface may further be manufactured from a moisture-wicking material, and the bottom surface is also preferably impermeable, such that any urine and/or feces cannot seep through the pad and into the inner surface. The edges of the pad may further be ridged or pleated to prevent urine and/or feces from spilling out from the pad and onto the inner surface when the pad is removed.

Referring initially to the drawings, FIG. 1 illustrates a front view of one embodiment of the reusable diaper with disposable pad device 100 of the present invention. The device 100 is comprised of a body 110 that has an outer surface 120 and an inner surface 150 (shown in FIG. 3), a rear surface 130 with at least two tabs 132, a front surface 140 with at least two tabs 142 and an inner surface 150 with at least one pad 200 (shown in FIG. 2). In differing embodiments, the body 110 of the device 100 may be manufactured of a plurality of materials such as, but not limited to, wood pulp, sodium polyacrylate fibers, plastic (i.e., cellulose, polypropylene, polyethylene etc.), tissue paper, non-woven fabric, non-permeable film, etc., or any other suitable diaper material as is known in the art or a combination thereof. In addition, the body 110 and/or all or some of the components of the device 100 may be infused with a plurality of substances unless otherwise stated, including, but not limited to, aloe vera, zinc oxide, calendula, lanolin, petroleum, and/or other moisturizing, anti-fungal, anti-bacterial compounds as are known in the art. Further, the material of the body 110 may be hypoallergenic and/or scented or non-scented.

The outer surface 120 may further have any number of indicia 152 such as, but not limited to, patterns, logos, emblems, images, symbols, designs, letters, words, characters, animals, advertisements, brands, etc., or any other suitable indicia as is known in the art. In addition, the body 110 has a pair of continuous leg openings 154 to allow the legs of a user to be placed through the body 110 while the device 100 is in use. The continuous leg openings 154 can be any suitable size as is known in the art, and can be sized to fit an infant, a small child and/or an adult, depending on the needs and/or wants of a user.

Furthermore, the at least two tabs 132, 142 of the rear surface 130 and front surface 140 are further each comprised of at least one fastener 160. In differing embodiments, the fastener 160 may be any suitable fastener as is known in the art, such as but not limited to, a hook and loop and/or adhesive, etc. Accordingly, the fastener 160 allows the tabs 132, 142 to adhere to one another, such that the body 110 of the device 100 can be secured around a user.

Figure 2:
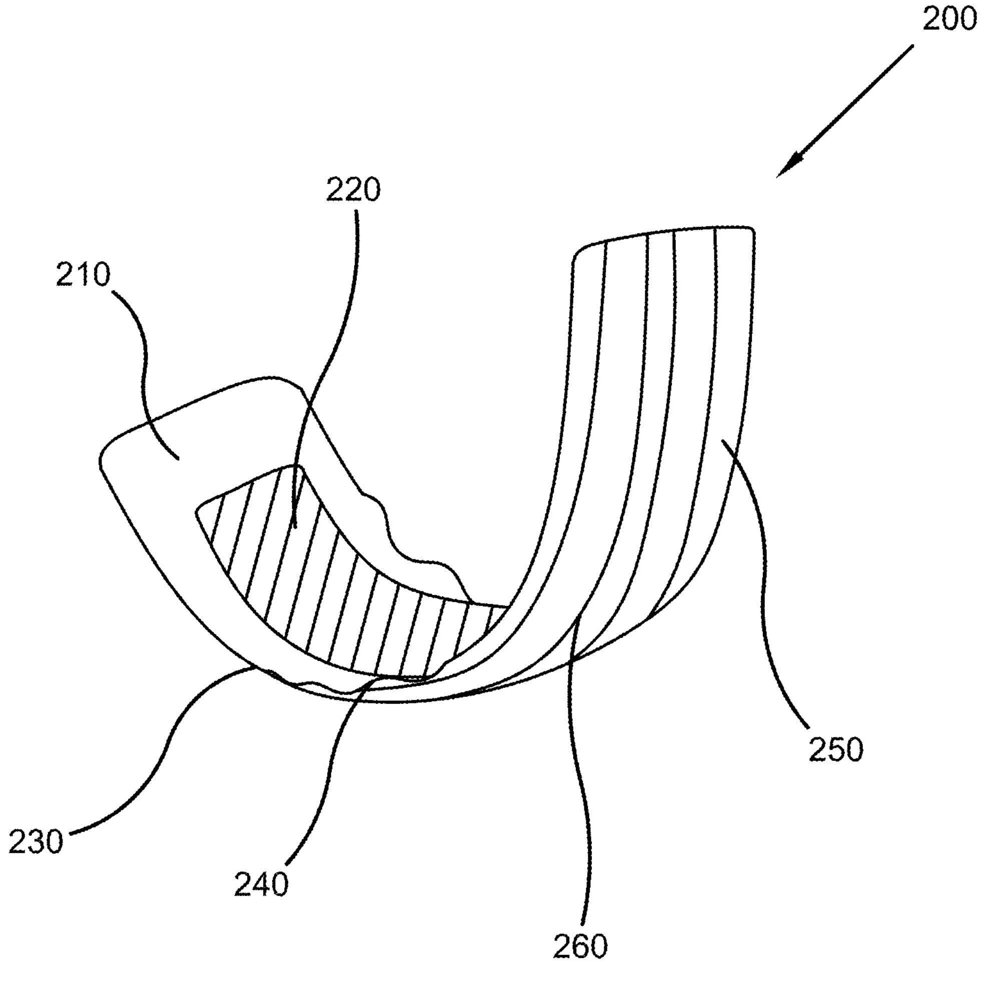
FIG. 2 illustrates a perspective view of one potential embodiment of the pad of the reusable diaper with disposable pad device of the present invention in accordance with the disclosed architecture.

FIG. 2 illustrates a perspective view of a pad 200 of the reusable diaper with disposable pad device 100 of the present invention. The pad 200 is preferably generally rectangular in shape, but can be any suitable shape as is known in the art. Further, the pad 200 is typically manufactured of the same material as the body 110, but can be manufactured of any suitable material as is known in the art. The bottom surface 250 of the pad 200 is further comprised of at least one fastener 260. The at least one fastener can be any suitable fastener as is known in the art such as, but not limited to, a hook and loop and/or adhesive fastener. In this manner, the pad 200 can be removably-attached to the inner surface 150, such that it can be removed from the inner surface 150 and replaced with another pad 200 when a user urinates and/or defecates on the pad 200.

Furthermore, the top surface 210 of the pad 200 may further have at least one reusable or disposable gel pad 220 that increases the comfort of the top surface 210 against a user's skin. The top surface 210 may further be infused with or may be coated with a lotion such as, but not limited to, aloe vera, zinc oxide, calendula, lanolin, petroleum, etc., and other suitable moisturizing, anti-fungal, or anti-bacterial compounds that prevent diaper rash, irritation, and/or infection. In one embodiment, the top surface 210 and/or bottom surface 250 may further be manufactured from a moisture-wicking material. The bottom surface 250 is also preferably impermeable, such that any urine and/or feces cannot seep through the pad 200 and into the inner surface 150. Further, at least two edges 230 of the pad 200 may be ridged or pleated 240 to prevent urine and/or feces from spilling out from the pad 200 and onto the inner surface 150 when the pad 200 is removed.

Figure 3:
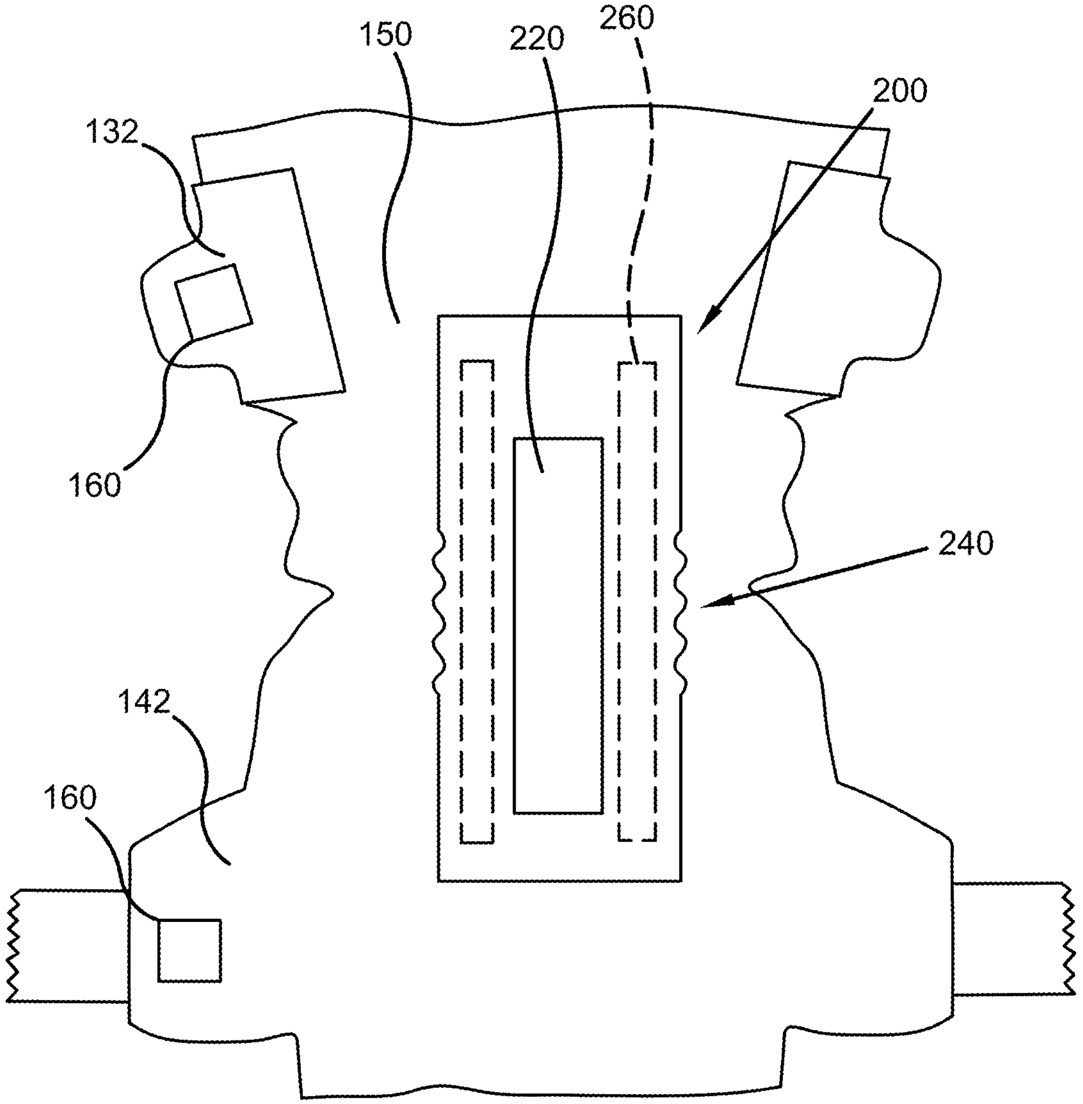
FIG. 3 illustrates a perspective view of one potential embodiment of the reusable diaper with disposable pad device of the present invention in an open position in accordance with the disclosed architecture.

As seen in FIG. 3, the inner surface 150 of the reusable diaper with disposable pad device 100 is further comprised of at least one absorbent pad 200. The pad 200 is further comprised of at least one fastener 260, which allows the pad 200 to be removably-attached to the inner surface 150, such that the pad 200 can be removed and replaced when needed. The top surface 210 may further have at least one reusable or disposable gel pad 220 that increases the comfort of the top surface 210 against a user's skin. At least two edges 230 of the pad 200 may further be ridged or pleated 240 to prevent urine and/or feces from spilling out from the pad 200 and onto the inner surface 150 when the pad 200 is removed.

Additionally, the rear surface 130 of the device 100 comprises at least two tabs 132, and the front surface 140 of the device 100 comprises at least two tabs 142 to secure the device around a user's body. Once the tabs 132 and 142 are secured, a pair of continuous leg openings 154 are formed to allow the legs of a user to be placed through the body 110 while the device 100 is in use. Further, the at least two tabs 132, 142 of the rear surface 130 and front surface 140 are each comprised of at least one fastener 160. Accordingly, the fastener 160 allows the tabs 132, 142 to adhere to one another, such that the body 110 of the device 100 can be secured around a user.

Certain terms are used throughout the following description and claims to refer to particular features or components. As one skilled in the art will appreciate, different persons may refer to the same feature or component by different names. This document does not intend to distinguish between components or features that differ in name but not structure or function. As used herein "reusable diaper with disposable pad device" and "device" are interchangeable and refer to the reusable diaper with disposable pad device 100 of the present invention.

Notwithstanding the forgoing, the reusable diaper with disposable pad device 100 of the present invention and its various components can be of any suitable size and configuration as is known in the art without affecting the overall concept of the invention, provided that they accomplish the above-stated objectives. One of ordinary skill in the art will appreciate that the size, configuration and material of the reusable diaper with disposable pad device 100 as shown in FIGS. 1-3 is for illustrative purposes only, and that many other sizes and shapes of the reusable diaper with disposable pad device 100 are well within the scope of the present disclosure. Although the dimensions of the reusable diaper with disposable pad device 100 are important design parameters for user convenience, the reusable diaper with disposable pad device 100 may be of any size, shape and/or configuration that ensures optimal performance during use and/or that suits the user's needs and/or preferences.

Various modifications and additions can be made to the exemplary embodiments discussed without departing from the scope of the present invention. While the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What has been described above includes examples of the claimed subject matter. It is, of course, not possible to describe every conceivable combination of components or methodologies for purposes of describing the claimed subject matter, but one of ordinary skill in the art may recognize that many further combinations and permutations of the claimed subject matter are possible. Accordingly, the claimed subject matter is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A reusable diaper with disposable pad device comprising:

a reusable body further comprised of a pair of leg openings, an inner surface and an outer surface comprising an image indicia;

a rear surface with at least two tabs;

a front surface with at least two tabs; and a disposable pad that attaches to the inner surface via at least one fastener;

wherein the reusable body is a wood pulp body; and wherein at least two edges of the disposable pad are pleated; and wherein the top surface of the disposable pad is infused with a calendula compound and an anti-fungal compound.

2. The reusable diaper with disposable pad device of claim 1, wherein the disposable pad can be removed from the inner surface and replaced with a second disposable pad when a user soils the disposable pad.

3. The reusable diaper with disposable pad device of claim 1, wherein a top surface of the disposable pad is further comprised of a gel pad.

4. A reusable diaper with disposable pad device comprising:

a reusable body further comprised of a pair of leg openings, an inner surface and an outer surface comprising an indicia, a rear surface with at least two tabs, and a front surface with at least two tabs; and a disposable pad that attaches to the inner surface via at least one fastener located on an impermeable bottom surface of the disposable pad, and wherein a top surface of the disposable pad is comprised of a gel pad;

wherein the reusable body is a sodium polyacrylate fiber body; and wherein at least two edges of the disposable pad are pleated; and wherein the top surface of the disposable pad is infused with a zinc oxide compound, a lanolin compound, and an anti-fungal compound.

5. The reusable diaper with disposable pad device of claim 4, wherein the disposable pad can be removed from the inner surface and replaced with a second disposable pad when a user soils the disposable pad.

6. The reusable diaper with disposable pad device of claim 4, wherein the at least one fastener is a hook and loop fastener or an adhesive fastener.

7. The reusable diaper with disposable pad device of claim 4, wherein the disposable pad is absorbent.

8. The reusable diaper with disposable pad device of claim 4, wherein the disposable pad is moisture wicking.

9. The reusable diaper with disposable pad device of claim 4, wherein the bottom surface of the disposable pad is impermeable.

10. A reusable diaper with disposable pad device comprising:

a reusable body further comprised of a pair of leg openings, an inner surface and an outer surface comprising an indicia, a rear surface with at least two tabs further comprised of at least one fastener, and a front surface with at least two tabs further comprised of at least one fastener; and a disposable pad that attaches to the inner surface via at least one fastener located on an impermeable bottom surface of the disposable pad, wherein a top surface of the disposable pad is comprised of a gel pad, and further wherein at least two edges of the disposable pad are pleated; and wherein the reusable body is hypoallergenic; and wherein the reusable body is a wood pulp and sodium polyacrylate fiber body; and wherein the top surface of the disposable pad is infused with an aloe vera compound, a zinc oxide compound, a calendula compound, a lanolin compound, and an anti-fungal compound.

11. The reusable diaper with disposable pad device of claim 10, wherein the disposable pad can be removed from the inner surface and replaced with a second disposable pad when a user soils the disposable pad.

12. The reusable diaper with disposable pad device of claim 10, wherein the reusable body is scented.

13. The reusable diaper with disposable pad device of claim 10, wherein the at least one fastener is a hook and loop fastener or an adhesive fastener.

14. The reusable diaper with disposable pad device of claim 10, wherein the at least two tabs of the rear surface can be attached to the at least two tabs of the front surface.

15. The reusable diaper with disposable pad device of claim 10, wherein the disposable pad is absorbent.

16. The reusable diaper with disposable pad device of claim 10, wherein the disposable pad is moisture wicking.

17. The reusable diaper with disposable pad device of claim 10, wherein the bottom surface of the disposable pad is impermeable.

* * * * *